United States Patent
Datta et al.

(10) Patent No.: US 7,507,224 B2
(45) Date of Patent: Mar. 24, 2009

(54) EASY-TO-UNFOLD FOLDED ABSORBENT GARMENT WITH DISTAL EDGES OF THE FRONT AND BACK WAIST REGIONS FOLDED ALONG RESPECTIVE LONGITUDINAL FOLD LINES

(75) Inventors: Paul Joseph Datta, Appleton, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 685 days.

(21) Appl. No.: 10/881,465

(22) Filed: Jun. 30, 2004

(65) Prior Publication Data

US 2006/0004343 A1    Jan. 5, 2006

(51) Int. Cl.
*A61F 13/15* (2006.01)
*A61F 13/20* (2006.01)

(52) U.S. Cl. ................................. 604/385.01
(58) Field of Classification Search ............ 604/385.01, 604/385.201, 358, 385.04, 385.21, 385.22, 604/385.23, 385.24, 385.25, 85.26, 385.27; D24/124; 428/152; 156/204
See application file for complete search history.

(56) References Cited

U.S. PATENT DOCUMENTS

| | | | | |
|---|---|---|---|---|
| 3,710,797 A | * | 1/1973 | Marsan ................. | 604/385.201 |
| 4,425,127 A | * | 1/1984 | Suzuki et al. ............... | 604/366 |
| 4,519,800 A | * | 5/1985 | Merry ..................... | 604/385.25 |
| 4,585,448 A | | 4/1986 | Enloe | |
| 4,601,717 A | * | 7/1986 | Blevins .................. | 604/385.27 |
| 5,599,338 A | * | 2/1997 | Enloe ..................... | 604/385.28 |
| 5,599,417 A | * | 2/1997 | Glaug et al. ................. | 156/227 |
| 5,858,515 A | | 1/1999 | Stokes et al. | |
| 6,165,160 A | * | 12/2000 | Suzuki et al. .......... | 604/385.201 |
| 6,626,881 B2 | | 9/2003 | Shingu et al. | |
| 2003/0078556 A1 | * | 4/2003 | Sasaki et al. ........... | 604/385.25 |

FOREIGN PATENT DOCUMENTS

EP    0 947 446 A1    10/1999
JP    04152947 A  *  5/1992

OTHER PUBLICATIONS

Trennepohl, Mike, Preparing a disposable garment for packaging, Research Disclosure Database No. 474005, Oct. 2003, p. 1.*

* cited by examiner

*Primary Examiner*—Michele Kidwell
(74) *Attorney, Agent, or Firm*—Dority & Manning, P.A.

(57) ABSTRACT

An absorbent garment, such as a diaper, folded in a manner that prevents leg elastics from remaining folded inward in a crotch region during product application. Each of two transversely opposed distal edges in a back waist region and each of two transversely opposed distal edges in a front waist region are folded onto a surface of the garment along respective longitudinal fold lines. The garment is also folded along at least one transverse fold line. A distance between the longitudinal fold lines in the back waist region may be greater than a distance between transversely opposed leg elastics in a crotch region of the garment. A distance between the longitudinal fold lines in the back waist region may be less than a combined distance between each of the transversely opposed distal edges of the back waist region and the respective longitudinal fold line.

39 Claims, 5 Drawing Sheets

EASY-TO-UNFOLD FOLDED ABSORBENT GARMENT WITH DISTAL EDGES OF THE FRONT AND BACK WAIST REGIONS FOLDED ALONG RESPECTIVE LONGITUDINAL FOLD LINES

BACKGROUND OF THE INVENTION

This invention is directed to an open absorbent garment that is folded for packaging in a manner that prevents leg elastics from remaining folded inward in a crotch region during product application.

Absorbent garments, such as diapers, are typically folded and packaged for most efficient use of space. Commercial diapers, for example, often include three folds, with two of the folds extending longitudinally from a front waist edge to a back waist edge along the left and right sides such that the front and back ears are folded onto the body side liner, and a third fold extending transversely such that the garment is folded in half. This folded configuration is uniform and easy to handle in packaging equipment. Additionally, packages of garments folded in this manner can be an effective size for shipment and for display on retail shelves.

One drawback of conventionally folded garments is that the garments may be difficult for parents or caregivers to open because, even after unfolding, the leg elastics and containment flaps may have a tendency to remain folded inward. The leg elastics and containment flaps often become fixed in place because adhesive can bleed through or be forced through the liner when subjected to packaging pressure. This adhesive tacks the folded leg ruffle to the liner. If the leg elastics remain tacked to the liner in the crotch area, the crotch portion of the leg ruffle will remain inboard the leg elastic in the crotch region and at some point the leg elastics will twist and cross over, thereby creating a leakage channel. The same adhesive may tack both the leg elastic and the containment flap to the liner.

Parents and other caregivers who recognize the need to manually unfold the leg elastics from within the crotch region often habitually shake out the garment, or run a finger under the leg elastics, in order to separate the leg elastics and containment flaps from the liner. The need for such an additional step adds time and effort to the garment-changing process.

There is thus a need or desire for an absorbent garment that is folded in such a manner that the garment can be applied after a single unfolding step without requiring the garment to be shaken and/or taking additional steps to separate the leg elastics from the liner and/or the containment flaps.

SUMMARY OF THE INVENTION

In response to the discussed difficulties and problems encountered in the prior art, a new folded configuration of an open absorbent garment has been discovered. This folded configuration obviates the need to perform extra steps or adjustments prior to applying the garment to a wearer. The principles of the invention may be applied to any of a number of personal care product applications, such as diapers, diaper pants, training pants, swimwear, adult incontinence products, and the like.

The absorbent garment of the invention includes an absorbent chassis that defines a waist opening and two leg openings when the garment is in a fastened position. The absorbent chassis may include an absorbent core positioned between an outer cover and a body side liner.

The garment has a longitudinal length extending from a front waist region to a back waist region, with each of two transversely opposed distal edges of the back waist region folded onto a surface of the absorbent chassis along respective longitudinal fold lines, and each of two transversely opposed distal edges of the front waist region folded onto a surface of the absorbent chassis along respective longitudinal fold lines. In addition to the longitudinal fold lines, the garment is also folded along at least one transverse fold line. The garment may be folded along a transverse fold line that folds the garment in half, thereby aligning the front waist region with the back waist region.

In certain embodiments, the distance between the longitudinal fold lines in the back waist region in a plan view (FIG. 3), which is the folded width of the garment, is less than a combined distance between each of the transversely opposed distal edges of the back waist region and the respective longitudinal fold lines. Thus, the transversely opposed distal edges of the back waist region may overlap one another on the surface of the absorbent chassis. This relationship is important as it improves the compactness of the packaged garment, thereby creating cost savings over conventional diapers. Compactness translates to a more consistently dense rectangular package of garments.

In certain embodiments, the distance between the longitudinal fold lines in the back waist region, or the folded width of the garment, may be greater than a distance between transversely opposed leg elastics in the crotch region of the absorbent chassis. Furthermore, the distance between the longitudinal fold lines in the back waist region may be greater than a distance between transversely opposed distal edges of the crotch region of the absorbent chassis. When the fold lines are outboard of the narrowest width of the crotch region, the fold lines do not extend through the entirety of the crotch region. Thus, the longitudinal fold lines in the back waist region may be discontinuous with the longitudinal fold lines in the front waist region. Additionally, portions of the transversely opposed distal edges of the crotch region may not be folded onto a surface of the absorbent chassis, but instead may extend outward from the garment in an unfolded state. More particularly, in certain embodiments, there may be no longitudinal fold lines in the absorbent chassis between the transversely opposed leg elastics across the narrowest width of the crotch region.

The absorbent garment may have a proportionally narrower crotch region than conventional absorbent garments, which facilitates the folded configuration of the absorbent garment and also creates a less bulky garment and package, which in turn increases packaging efficiency through a reduction in packaging materials. The proportionality of the crotch region can be assessed with respect to an expanded width of the absorbent chassis measured between the transversely opposed distal edges of the back waist region. Thus, in certain embodiments, the absorbent chassis may have an elasticized-crotch-to-waist ratio of about 0.35 or less with the elasticized-crotch-to-waist ratio being a narrowest distance between two transversely opposed leg elastics in the crotch region divided by the expanded width of the absorbent chassis. Low crotch-to-waist ratios reduce the chances of adhesive bleed-through since the leg elastics are not pressed against the absorbent core in the folding and packaging operations. Another measurement of crotch region proportionality is a crotch-to-waist ratio. More particularly, the absorbent chassis may have a crotch-to-waist ratio of about 0.55 or less with the crotch-to-waist ratio being the narrowest distance between transversely opposed distal edges in the crotch region divided by the expanded width of the absorbent chassis. Yet another measurement of crotch region proportionality is an absorbent-to-waist ratio. More particularly, the absorbent chassis may have an absorbent-to-waist ratio of about 0.47 or less with the absorbent-to-waist ratio being a widest width of the absorbent core divided by the expanded width of the absorbent chassis. All measurements of noted dimensions are made when the absorbent garment is in the flat state, shown in FIG. 3, with the elastics inactivated or removed; however, measurements of the longitudinal fold lines are marked at the longitudinal midpoint of the folded garment prior to unfolding to the flat state to assure that the elastic materials do not distort the manufactured fold lines.

An absorbent garment, in accordance with the invention, can be folded by folding each of the transversely opposed distal edges of the back waist region onto a surface of the absorbent chassis along respective longitudinal fold lines, and folding each of the transversely opposed distal edges of the front waist region onto a surface of the absorbent chassis along respective longitudinal fold lines, and folding the absorbent chassis along at least one transverse fold line. The folding should be performed in such a manner that a distance between the longitudinal fold lines in the back waist region is greater than the distance between transversely opposed leg elastics in the crotch region, for example.

The folded absorbent garments can be packaged in the folded position. Thus, the invention also includes packages of the folded absorbent garments.

With the foregoing in mind, it is a feature and advantage of the invention to provide a folded absorbent garment having strategically positioned fold lines to assure that materials are not folded over in the crotch region, thereby preventing leakage channels that may be formed from folding and/or adhesive that can accidentally bleed through and tack the leg elastics down.

BRIEF DESCRIPTION OF THE DRAWINGS

These and other objects and features of this invention will be better understood from the following detailed description taken in conjunction with the drawings, wherein.

DEFINITIONS

Within the context of this specification, each term or phrase below will include the following meaning or meanings.

"Absorbent garment" includes personal care garments, medical garments, and the like. The term "disposable garment" includes garments that are typically disposed of after 1-5 uses. The term "personal care garment" includes diapers, diaper pants, training pants, swimwear, absorbent underpants, adult incontinence products, feminine hygiene products, and the like.

"Attached" refers to the joining, adhering, connecting, bonding, or the like, of at least two elements. Two elements will be considered to be attached together when they are attached directly to one another or indirectly to one another, such as when each is directly attached to intermediate elements.

"Fold line" refers to a crease resulting from one section of a continuous object folded onto another section of the same object. Insignificant wrinkles in materials from processing are not considered to constitute fold lines.

Figure 2:
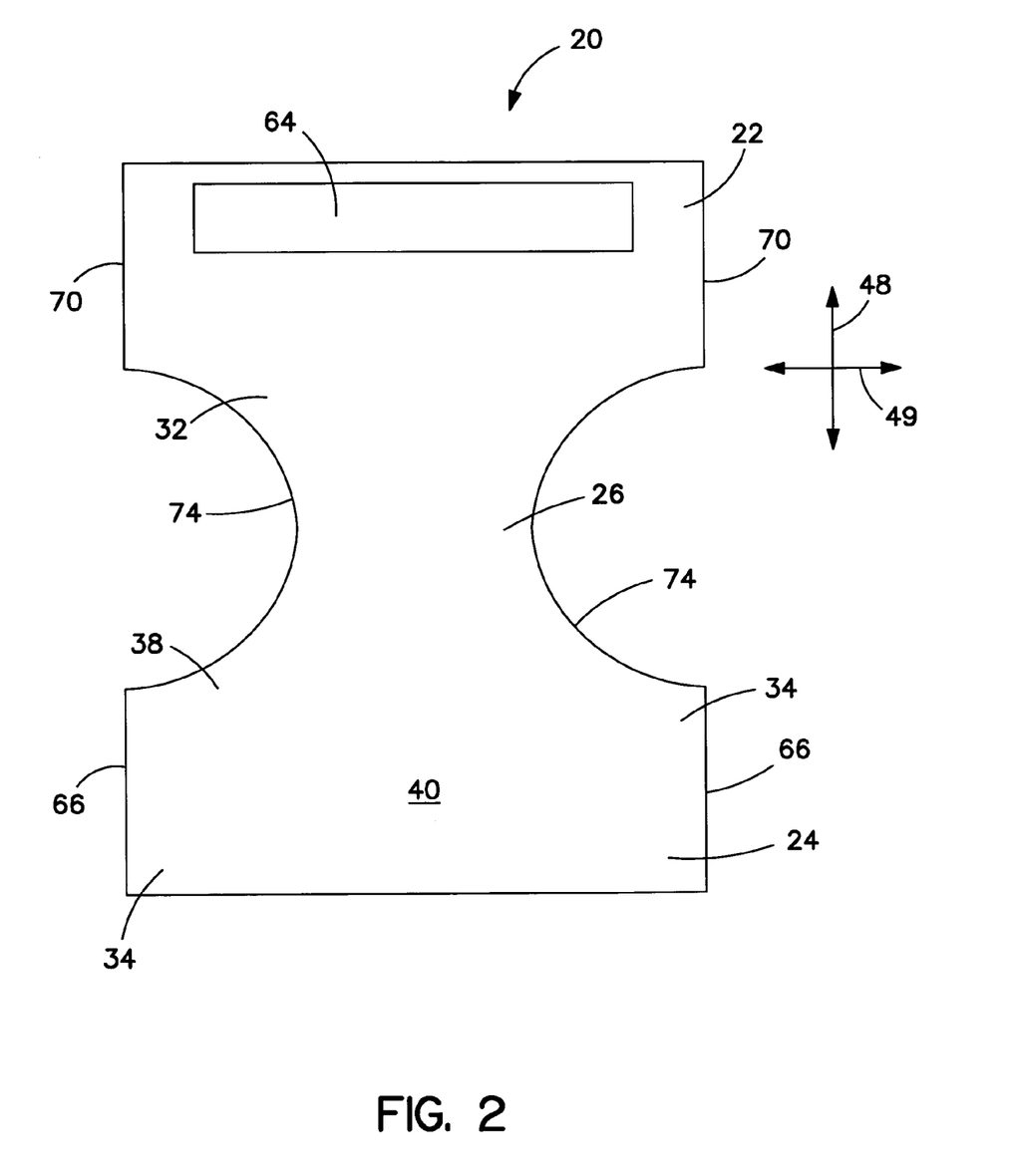
FIG. 2 is a plan view of an absorbent garment similar to the absorbent garment of FIG. 1 in a stretched flat state, and showing the surface of the garment that faces away from the wearer when the garment is worn.
Figure 3:
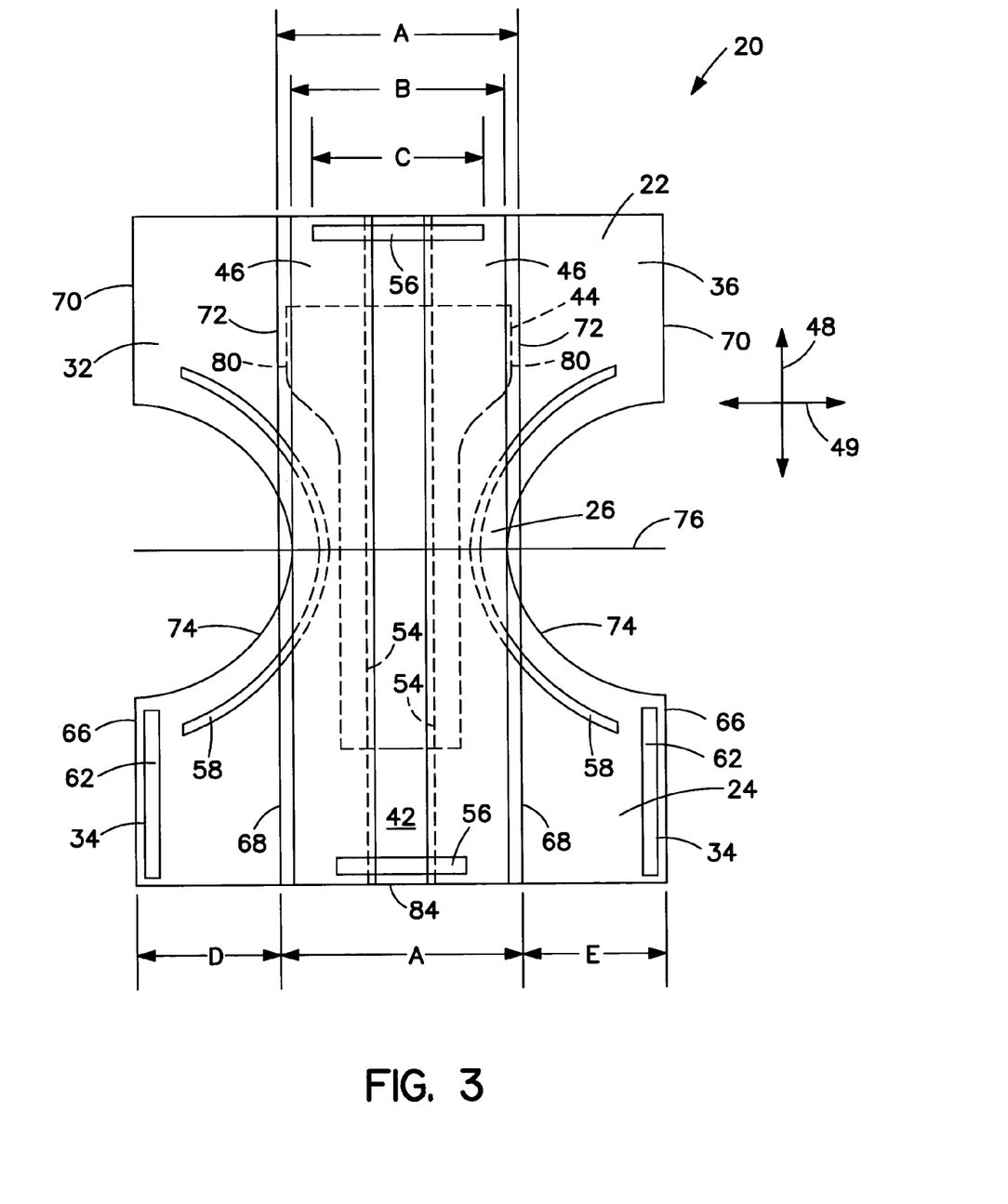
FIG. 3 is a plan view of an absorbent garment similar to the absorbent garment of FIG. 1 in a stretched flat state, and showing the surface of the garment that faces the wearer when the article is worn.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Open diaper" and "open absorbent garment" refer to diapers and other absorbent garments that are not prefastened. More particularly, these open garments do not have their front and back panels fastened, or attached to one another, when in the packaged state. Open diapers and absorbent garments require a caregiver to fasten the front waist region to the back waist region either before or during the process of applying the garment to a wearer.

"Transversely opposed distal edges" refer to the outermost or most outboard edges of an object that define, in part, the perimeter of the object along opposite edges of the garment, such that a line drawn from one edge to the opposite edge is parallel to a transverse axis of the object.

These terms may be defined with additional language in the remaining portions of the specification.

DESCRIPTION OF PREFERRED EMBODIMENTS

In accordance with the invention, a folded absorbent garment having strategically located fold lines prevents materials from remaining folded over in the crotch region when the garment is applied to a wearer.

The principles of the present invention can be incorporated into any suitable pant-like disposable absorbent garment. Examples of such suitable garments include diapers, diaper pants, training pants, incontinence products, other personal care or health care garments, including medical garments, or the like. For ease of explanation, the description hereafter will be in terms of a diaper.

Figure 1:
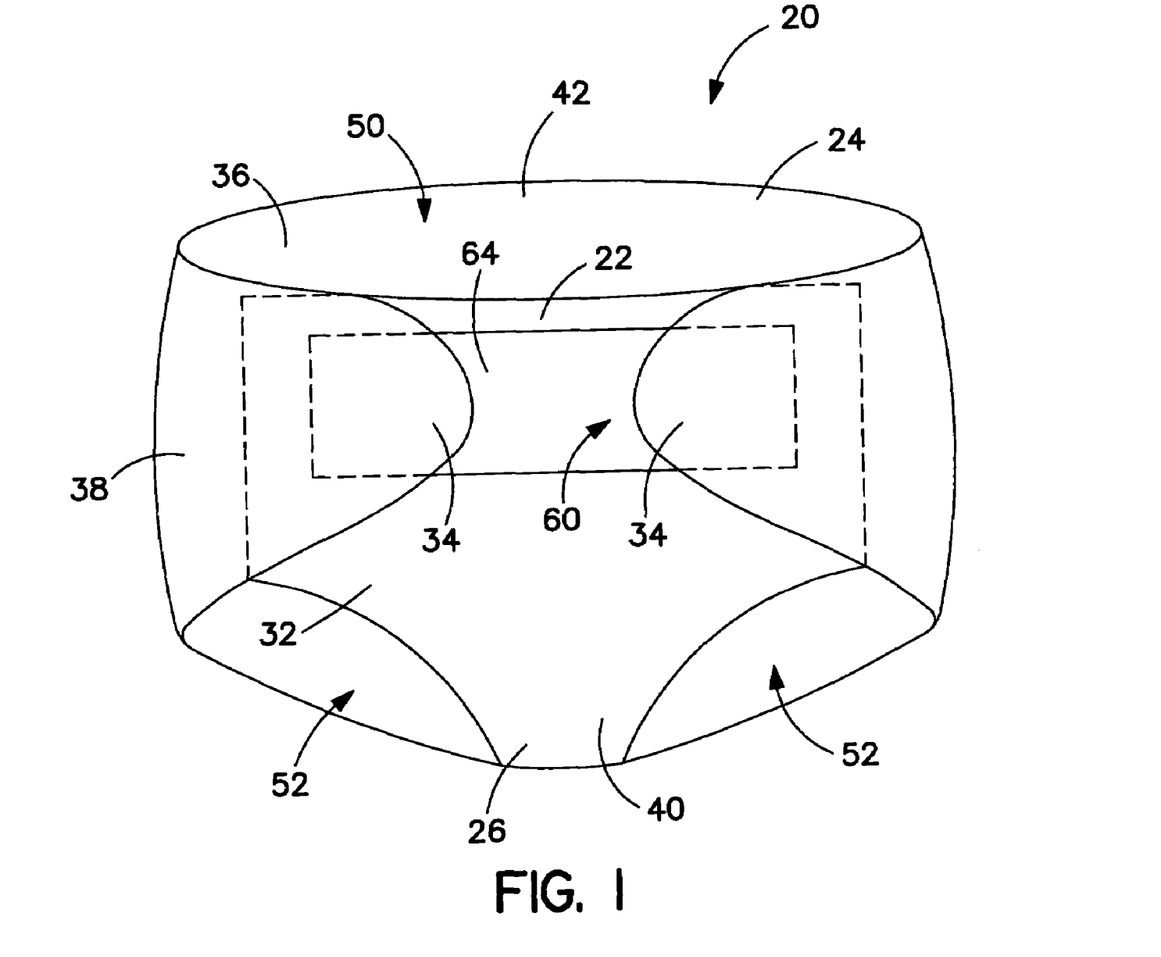
FIG. 1 is a perspective view of an absorbent garment, such as a diaper, unfolded and in a fastened position.

Referring to FIG. 1, a diaper 20 is illustrated in a fastened position as the garment would appear when worn. FIGS. 2 and 3 illustrate the diaper 20 in a stretched flat state in which the various dimensions of the garment are measured. More particularly, FIG. 2 is a view of a garment-facing outer surface 38 of the diaper 20, and FIG. 3 is a view of a body-facing inner surface 36 of the diaper 20. The diaper 20 includes an absorbent chassis 32 defining a front waist region 22, a back waist region 24, and a crotch region 26 interconnecting the front and back waist regions. In the fastened position, the absorbent chassis 32 defines a three-dimensional pant configuration having a waist opening 50 and a pair of leg openings 52. The chassis 32 includes a body side liner 42 which is configured to contact the wearer, and an outer cover 40 opposite the body side liner which is configured to contact the wearer's clothing. An absorbent core 44 (FIG. 3) is positioned or located between the outer cover 40 and the body side liner 42. The absorbent core 44 has a shorter length and width than the outer cover 40 and body side liner 42 and is spaced inboard from all edges of the outer cover 40 and body side liner 42.

The front waist region 22 includes the portion of the diaper 20 which, when worn, is positioned on the front of the wearer while the back waist region 24 includes the portion of the diaper which, when worn, is positioned on the back of the wearer. The crotch region 26 of the diaper 20 includes the portion of the diaper which, when worn, is positioned between the legs of the wearer and covers the lower torso of the wearer.

The waist regions 22, 24 are configured to encircle the waist of the wearer when the diaper 20 is worn. A longitudinal length of the absorbent chassis 32 is the distance between (and including) the front waist region 22 and the back waist region 24. For reference, arrows 48 and 49 depicting the orientation of the longitudinal axis and the transverse axis, respectively, of the diaper 20 are illustrated in FIGS. 2 and 3.

The diaper 20 can be folded in accordance with the invention by folding each of two transversely opposed distal edges 66 of the back waist region 24 onto a surface of the absorbent chassis 32, namely the inner surface 36 or the outer surface 38, along respective longitudinal fold lines 68, and folding each of two transversely opposed distal edges 70 of the front waist region 22 onto a surface of the absorbent chassis 32 along respective longitudinal fold lines 72. Referring to FIG. 3, the distance between the longitudinal fold lines 70 is the distance "A," the narrowest distance between transversely opposed distal edges 74 of the crotch region 26 is the distance "B," and the narrowest distance between transversely opposed leg elastics 58 is the distance "C." The distance between the transversely opposed leg elastics 58 is measured from an outermost edge of an outermost leg elastic closest to the distal edge 74 of the crotch region 26 on each side of the crotch region 26. For example, if the leg elastics 58 each include multiple strands of elastic, the distance between transversely opposed leg elastics 58 is measured from an outermost edge of the strand closest to the distal edge 74 of on one side of the crotch region 26 to an outermost edge of the strand closest to the distal edge 74 on the other side of the crotch region 26. Once the distal edges 70, 66 of the front and back waist regions 22, 24 have been folded, the absorbent chassis 32 can then be folded along at least one transverse fold line 76, thereby encasing the distal edges 70, 66 of the front and back waist regions 22, 24 inside the folded absorbent chassis 32. The folded absorbent garments can then be stacked, in stacks of about 2 to about 75 diapers, for example, so that each adjacent pair of diapers contacts one another along a planar portion of their outer covers 40.

As shown in FIG. 3, the distance (A) between the longitudinal fold lines 68 in the back waist region 24 may be greater than the narrowest distance (C) between transversely opposed leg elastics 58 in the crotch region 26. These distances are measured when the diaper is stretched flat in the plan view as shown in FIG. 3. In certain embodiments the longitudinal fold lines 68 may be parallel to one another in the plan view. In other embodiments the longitudinal fold lines 68 may be non-parallel to one another and/or may curve. In all instances, the distances between the longitudinal fold lines 68 should be measured 100 mm from the back waist edge 84 of the absorbent garment 20.

Additionally, as also shown in FIG. 3, the distance (A) between the longitudinal fold lines 68 in the back waist region 24 may be greater than the narrowest distance (B) between the distal edges 74 of the crotch region 26. Thus, portions of the distal edges 74 of the crotch region 26 may not be folded onto a surface of the absorbent chassis 32, but instead a portion of the crotch region 26 may remain essentially planar, or unfolded, across a transverse width of the crotch region 26. In certain embodiments, the narrowest width (C) between the transversely opposed leg elastics 58 in the crotch region 26 may be free of any longitudinal fold lines. Furthermore, the narrowest width (B) between the distal edges 74 of the crotch region 26 may be free of any longitudinal fold lines. Thus, the longitudinal fold lines 68 in the back waist region 24 may be discontinuous with the longitudinal fold lines 72 in the front waist region 22 due to the lack of longitudinal fold lines in at least a portion of the crotch region 26.

Figure 4:
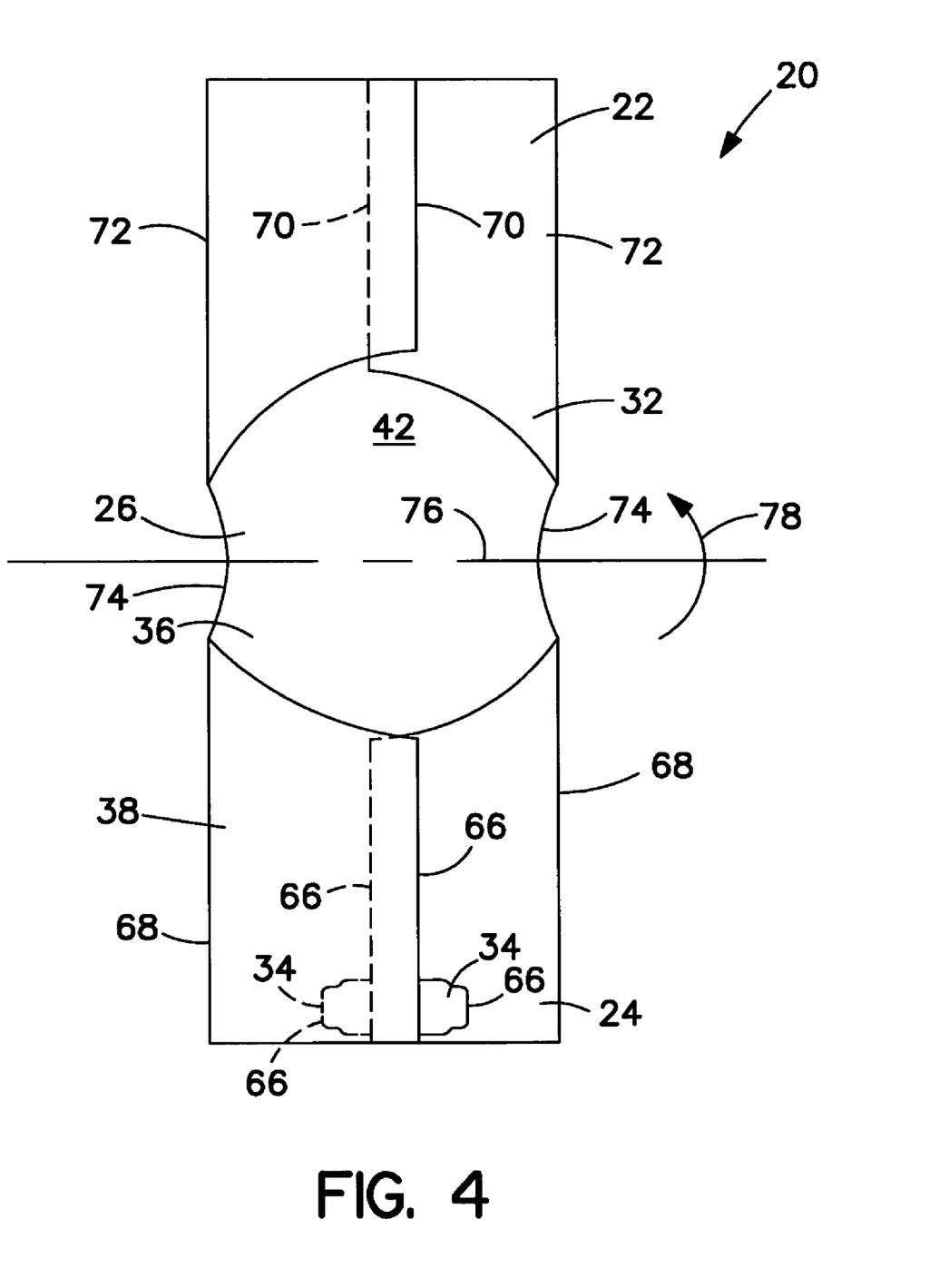
FIG. 4 is a plan view of an absorbent garment similar to the absorbent garment of FIG. 3 in a partially folded state, according to at least one embodiment of this invention.

Still referring to FIG. 3, the distances between the transversely opposed distal edges 66 of the back waist region 24 and the respective longitudinal fold lines 68 are marked as distances "D" and "E." Suitably, the distance between the longitudinal fold lines 68 in the back waist region (A) may be less than the combined distances D and E. Additionally or alternatively, the distance between the longitudinal fold lines 72 in the front waist region 22 may be less than the combined distances between the transversely opposed distal edges 70 of the front waist region 22 and the respective longitudinal fold lines 72. In such embodiments, when the transversely opposed distal edges 66 of the back waist region 24 (and/or front waist region 22) are folded onto a surface of the absorbent chassis 32, the transversely opposed distal edges 66 may overlap one another, as shown in FIG. 4. This configuration provides for efficient packaging by creating relatively consistent thickness in the folded diaper 20, which allows the garments to be packaged relatively densely in a conventionally shaped package.

When measuring the distances between distal edges, care must be taken to unfold all folded components, ears, and fasteners to assure the absorbent garment is in its plan view. Pins may be used to hold the garment in a configuration in which any gathers and wrinkles are smoothed. Elastic components may be deadened or removed to achieve this plan view of the absorbent article after manufacture and packaging.

Once the distal edges 70, 66 of the front and back waist regions 22, 24 have been folded inward, the absorbent chassis 32 can be folded along a transverse fold line 76 in the direction of the arrow 78 illustrated in FIG. 4, thereby aligning the front waist region 22 with the back waist region 24 in a facing relationship. Alternatively, the absorbent chassis 32 may be folded along more than one transverse fold line 76, such as in a tri-fold configuration along two transverse fold lines, or other single- or multi-fold configurations.

The lengths, widths, and other linear distances measured herein are measured when the diaper 20 is in the developed flat state, as shown in FIG. 3. For measuring, the fold lines are marked at half the folded garment length, to assure the lines marking the fold lines cross a region 100 mm from the back waist edge 84, before fully opening the garment to the flat state in order to assure that the elastic materials within the garment do not distort the manufactured fold lines.

The illustrated absorbent chassis 32 includes a pair of transversely opposed eat panels or tabs 34, which extend transversely outward along the back waist region 24 of the absorbent chassis 32. The tabs 34 may be integrally formed with the outer cover 40 and/or the body side liner 42, as shown in FIGS. 2 and 3, or may include two or more separate elements, as shown in FIG. 4. Additionally, the tabs 34 may include a stretchable and/or elastomeric material capable of stretching in a direction generally parallel to the transverse axis 49 of the diaper 20. Additionally, one or more of the chassis materials may be composed of an elastic material, in which case the addition of elastic strands or other elastic materials may not be necessary to deliver the required retraction force to hold the absorbent garment up on the wearer. An expanded width of the absorbent chassis 32 can be measured according to the test method described in detail below. The dimensions "D" and "E" described above, as well as the expanded width of the absorbent chassis 32, include the lateral width of any attached components in the developed state of the garment. The expanded width of the absorbent chassis 32 measured in this manner provides an indication of the size of the garment with respect to a size of an intended wearer.

The absorbent garment 20 of the invention may have a narrow crotch region 26 compared to conventional absorbent garments, but the expanded width of the absorbent chassis 32 has not been reduced in the absorbent garment 20 of the invention compared to conventional absorbent garments. Thus, the expanded width of the absorbent chassis 32 can be used as a general garment size indicator when comparing garments of this invention to conventional absorbent garments to ensure that the garments being compared are intended to fit wearers of approximately the same size. A narrower crotch region 26 is conducive to folding the garment in the manner described herein, and a narrower crotch region 26 also improves the fit of the garment on a wearer by reducing the bulkiness between the wearer's legs. By "narrow crotch" it is meant that the distance between the leg elastics and/or the crotch width of the chassis is narrow. More specifically, the garment 20 of the invention may have a crotch region width that is proportional to one or more other dimensions of the absorbent chassis 32 in a manner that does not hold true for currently available commercial diapers. The proportionally narrow crotch in view of the size of the wearer, combined with the strategically positioned fold lines, delivers a packaged absorbent article with optimal packing design, superior fit in the crotch region, ease of use, and a reduced leakage feature described above. A wide crotch may cause the leg elastics to fold over during application, while narrow fold line spacing may cause the leg elastics to remain tacked down during packaging, both of which increase the likelihood of leakage. Thus, the narrow crotch and the strategic position of the fold lines work together to assure that folded elastics do not fold over to create leakage channels.

The width of the crotch region 26 is measured across the narrowest transverse width of the crotch region 26 between distal edges 74 when the diaper 20 is in a laid flat state with any elastic components either removed or otherwise disabled to prevent any interference with the crotch width measurement, similar to the expanded width measurement test method described below.

In certain embodiments, the absorbent garment 20 has a relatively low crotch-to-waist ratio. The crotch-to-waist ratio is the narrowest distance (B) between the transversely opposed distal edges 74 in the crotch region 26 divided by the expanded width of the absorbent chassis 32 measured between the transversely opposed distal edges 66 of the back waist region 24. The crotch-to-waist ratio is an indication of narrowness of the overall crotch region 26 of the garment in proportion to the overall size of the garment, with a lower crotch-to-waist ratio indicating a narrower crotch region 26. Suitably, the crotch-to-waist ratio is about 0.55 or less, or about 0.5 or less, or about 0.45 or less, or about 0.35 or less, or about 0.25 or less.

In at least another embodiment, the absorbent garment 20 has a relatively low elasticized-crotch-to-waist ratio. The elasticized-crotch-to-waist ratio is the narrowest distance (C) between the outermost transversely opposed leg elastics 58 in the crotch region 26 divided by the expanded width of the absorbent chassis measured between the transversely opposed distal edges 66 of the back waist region 24. The elasticized-crotch-to-waist ratio is an indication of the narrowness of the crotch region 26 between the elasticized portions in the crotch region 26 in proportion to the overall size of the garment, with a lower elasticized-crotch-to-waist ratio indicating a narrower elasticized crotch region 26. Suitably, the elasticized-crotch-to-waist ratio is about 0.35 or less, or about 0.3 or less, or about 0.25 or less, or about 0.2 or less, or about 0.15 or less.

In at least one other embodiment, the absorbent garment 20 has a relatively low absorbent-to-waist ratio. The absorbent-to-waist ratio is the widest width of the absorbent core 44 divided by the expanded width of the absorbent chassis 32 measured between the transversely opposed distal edges 66 of the back waist region 24. The absorbent-to-waist ratio is an indication of the narrowness of the absorbent core 44 in proportion to the overall size of the garment, with a lower absorbent-to-waist ratio indicating a narrower absorbent core 44. The widest width of the absorbent core 44 is measured from distal edge 80 to distal edge 80 of the absorbent core 44 in the transverse direction in a laid flat position across the widest transverse width of the absorbent core 44, negating any elastomeric effects from other components in the diaper 20. Suitably, the absorbent-to-waist ratio is about 0.47 or less, or about 0.42 or less, or about 0.37 or less, or about 0.32 or less, or about 0.27 or less.

The folded absorbent garment of the invention may include one or more of the embodiments described herein. The Example below compares the dimensions of commercially available diapers with two samples of absorbent garments of the invention.

The absorbent core 44 can be any structure which is generally compressible, conformable, non-irritating to the wearer's skin, and capable of absorbing and retaining liquids and certain body wastes at anticipated levels despite the narrowed crotch width. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The absorbent core 44 can have variable thickness, with greater thickness in "target" areas, such as in a central portion of the crotch region. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area. The absorbent core 44 may or may not be wrapped or encompassed by a suitable tissue wrap that maintains the integrity and/or shape of the absorbent core 44. In certain embodiments, the absorbent core 44 may contain a body side liner and/or a moisture barrier in addition to absorbent and distribution elements. In such embodiments, the absorbent core 44 may be attached to the outer cover 40 and need not be sandwiched between two layers. The absorbent core 44 may also contain leg elastics in embodiments such as this.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Degussa Superabsorber in Greensboro, N.C., U.S.A. Typically, a superabsorbent material is capable of absorbing at least about 15 times its weight in water, and desirably is capable of absorbing more than about 25 times its weight in water.

The absorbent chassis 32 can also incorporate other materials that are designed primarily to receive, temporarily store, and/or transport liquid along the mutually facing surface with the absorbent core 44, thereby maximizing the overall absorbent capacity of the absorbent core 44, if desired. One suitable material is referred to as a surge layer (not shown), which may be positioned between the absorbent core 44 and the body side liner 42 to manage incoming fluid. Additionally, a vapor-permeable, hydrophobic spacer layer (not shown) may be positioned between the absorbent core 44 and the outer cover 40 as a further measure to prevent a clammy feeling on an outer surface of the outer cover 40 when the garment is loaded.

In yet another embodiment, the absorbent garment 20 includes a waist elastic member 56 in the front waist region 22, in the back waist region 24, or in both the front and back waist regions 22, 24 of the garment, operatively attached to the outer cover 40 and/or body side liner 42 and extending across part or a full length of the waist regions.

To further enhance containment and/or absorption of body exudates, the diaper 20 may also include leg elastic members 58, as are known to those skilled in the art, described above with respect to FIG. 3. The leg elastic members 58 may be operatively joined to the outer cover 40 and/or body side liner 42 along opposite side edges of the absorbent chassis 32 and positioned in the crotch region 26 of the diaper 20.

The waist elastic members 56 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 56 may include a polystyrene-polyethylene-polypropylene-polystyrene (SEPS) block copolymer, such as KRATON® G2760, available from Kraton Inc. of Houston, Tex., U.S.A.

The diaper 20 may be refastenable, thereby including a refastenable fastening system 60 (FIG. 1) for securing the diaper about the waist of the wearer. One example of a suitable refastenable fastening system 60 may include fastening components 62, such as hook components, located along or adjacent to the distal edges 66 of the tabs 34. Suitable single-sided hook materials are available from Velcro Industries B.V., Amsterdam, Netherlands, or affiliates thereof. The fastening components 62 are adapted to refastenably connect to mating fastening components 64, such as loop material, located on an outer surface of the front waist region 22. One example of suitable loop material is "point unbonded" material. Point unbonded materials are fabrics having continuous thermally bonded areas defining a plurality of discrete unbonded areas and are described in greater detail in U.S. Pat. No. 5,858,515 issued Jan. 12, 1999 to Stokes, et al., incorporated herein by reference. The engaging elements of the fastening components 62 are adapted to repeatedly engage and disengage the engaging elements of the mating fastening components 64.

The outer cover 40 desirably includes a material that may be substantially liquid impermeable or liquid permeable, and can be elastic, stretchable, extensible, non-stretchable, or non-extensible. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer of the outer cover 40 desirably includes a material that can be elastic, stretchable, extensible, non-stretchable, or non-extensible. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain "non-breathable" elastic films can also be used to make the outer cover 40. Examples of suitable non-breathable films can be made of styrene-ethylene-butylene-styrene or styrene-isoprene-styrene block copolymers, KRATON® polymers from Kraton Inc. of Houston, Tex., U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent core 44, and may but need not have the same dimensions as the outer cover 40. The body side liner 42 is desirably compliant, soft feeling, and non-irritating to the wearer's skin. Further, the body side liner 42 can be less hydrophilic than the absorbent core 44, to present a relatively dry surface to the wearer and permit liquid to readily penetrate through its thickness. The body side liner 42 desirably includes a material that can be elastic, stretchable, extensible, non-stretchable, or non-extensible.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from available from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include extendible and/or elastomeric materials, it can be desirable in some embodiments for the composite structure to be generally inelastic, where the outer cover, the body side liner and the absorbent core include materials that are generally not elastomeric.

To enhance containment and/or absorption of any body exudates discharged from the wearer, the chassis 32 may include a pair of containment flaps 46 which are configured to provide a barrier to the transverse flow of body exudates. A flap elastic member 54 (FIG. 3) may be operatively joined with each containment flap 46 in any suitable manner as is well known in the art. The elasticized containment flaps 46 define an unattached edge which assumes an upright, generally perpendicular configuration in at least the crotch region 26 of the diaper 20 to form a seal against the wearer's body. The containment flaps 46 can be located along the transversely opposed side edges of the chassis 32, or in the crotch region 26, and can extend longitudinally along the entire length of the chassis or may only extend partially along the length of the chassis. Suitable constructions and arrangements for the containment flaps 46 are generally well known to those skilled in the art.

As described herein, the various components of the absorbent garment 20 can be integrally assembled together employing various types of suitable attachment means, such as adhesive, sonic and thermal bonds or combinations thereof.

Figure 5:
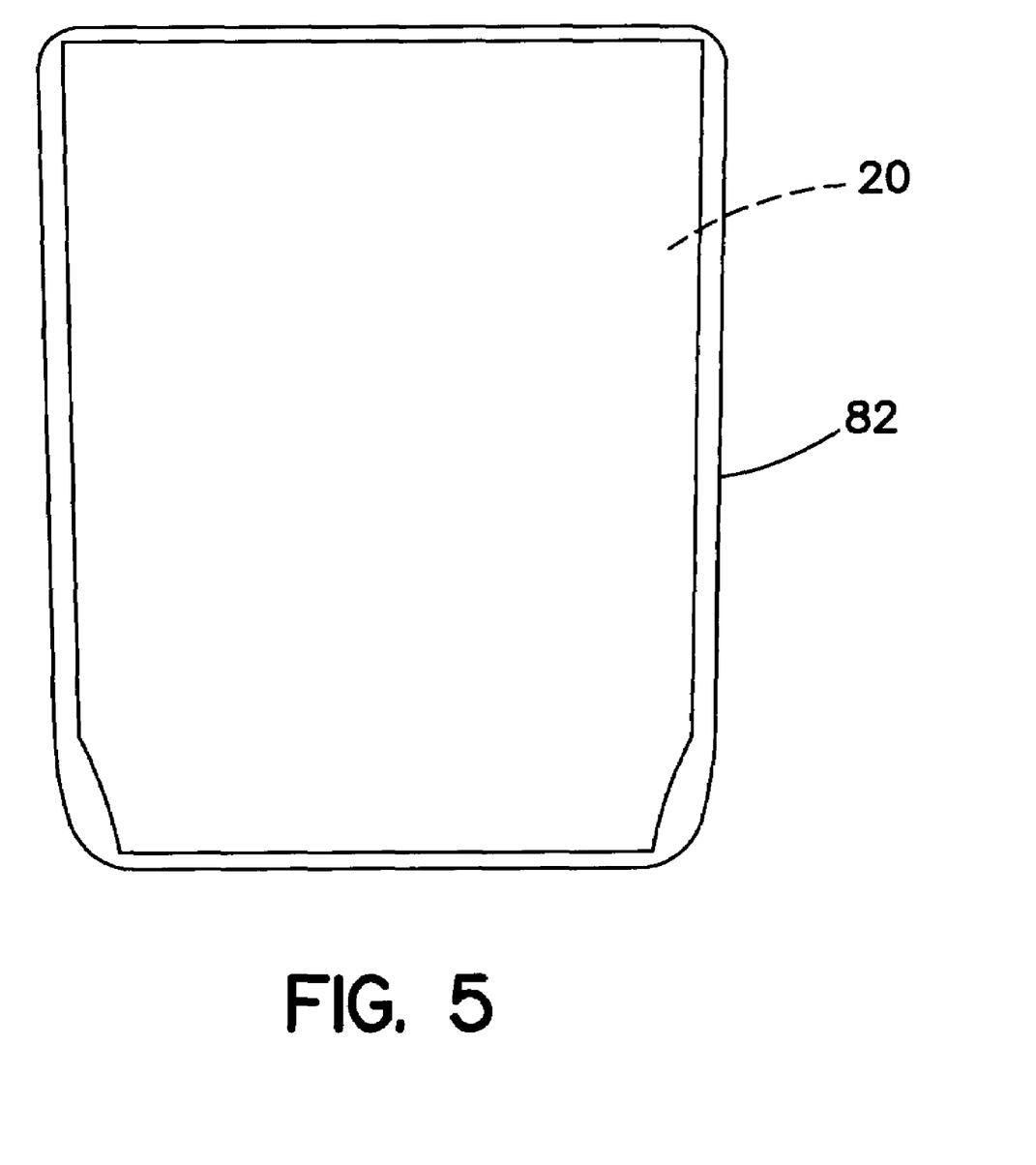
FIG. 5 is a plan view of an absorbent garment similar to the absorbent garment of FIG. 3 in a folded state and inside a package, according to at least one embodiment of this invention.

The folded absorbent garment can be packaged individually, or multiple folded absorbent garments can be packaged together in suitable packaging, such as in bags or boxes constructed of paper or polymeric film, for example. A package 82 containing the folded absorbent garment 20 is illustrated in FIG. 5. The packages 82 may contain any number of folded absorbent garments 20. As described above, the folded absorbent garments may be stacked so that each adjacent pair of garments contacts one another along a planar portion of their outer covers. These stacks may be packaged together such that a package contains multiple stacks of folded absorbent garments.

EXAMPLE

Two sample diapers were formed in accordance with the invention. Relevant dimensions of the sample diapers are provided in Table 1, along with comparative data from commercially available diapers. The two sample diapers were formed from the same materials as in HUGGIES Ultratrim Step 4 diapers, available from Kimberly-Clark Corporation of Neenah, Wis., and differed only by the dimensions shown in Table 1.

TABLE 1

Comparative Diaper Dimensions

| Diaper | Crotch Region Width (mm) | Narrowest Distance Between Leg Elastics (mm) | Distance Between Longitudinal Fold Lines (mm) |
|---|---|---|---|
| Sample 1 | 120 | 115 | 130 |
| Sample 2 | 115 | 110 | 120 |
| HUGGIES Ultratrim Step 4 | 195 | 156 | 115 |
| PAMPERS Custom Fit Cruisers Step 4 | 211 | 183 | 112 |
| WHITE CLOUD Step 4 | 196 | 177 | 115 |

Test Methods

Expanded Width Measurement Test Method

A suitable method for determining the expanded width of the absorbent chassis (32) is to hang the product vertically adjacent a flat, smooth, vertical surface. One example of a suitable surface is a 0.25-inch thick acrylic plastic sheet available from Eagle Plastics and Supply of Appleton, Wis. Prior to hanging, the product is opened by opening any fasteners, cutting or opening any side seams, and unfolding any folded portions to make the absorbent garment flat, as shown in the plan views of FIGS. 2 and 3. Any elastic components that run the width of the chassis (such as waist elastics) are severed at least once per inch along their entire length. The product is hung with one distal edge (66) above the transversely opposed distal edge (66) of the back waist region (24) and with the surface intended to face the wearer's outer garments during use positioned toward the flat, vertical surface. The top end margin of the product is held horizontal with two clamps, the inner edges of which are spaced 3.5 inches (8.9 cm) apart, or a single clamp if the tab (34) is shorter than 3.5 inches (8.9 cm) in length.

The lower end of the hanging product is clamped with a jig weighing 1500 grams. The jig possesses two clamp units (medium size, Bulldog clips, 2⅛ inch) attached to a tie rod (0.25-inch—20×12 inches, coarse thread, zinc plated), or a single clamp if the tab (34) is shorter than 3.5 inches (8.9 cm) in length, the clamps symmetrically placed with respect to the longitudinal centerline of the product, with a spacing between internal edges of the clamps of 3.5 inches (8.9 cm), with a 0.25-inch nut placed at the inner and outer edges of each clamp to hold the clamps in place. One (capped) bottle (1-ounce plastic screw cap bottle, such as NALGENE brand) is attached to each clamp with a piece of string. The assembly is placed on a laboratory balance and lead shot (No. 5 chilled lead shot, such as LAWRENCE brand) is added to each bottle (in equal amounts) until the total weight of the jig is as close to 1500 grams as possible. The jig is attached to the lower end of the hanging product adjacent the distal edge (66), as mentioned above.

For a typical product, a load of 1500 grams is appropriate. The expanded width of the back waist region (24) of the absorbent chassis (32) is then determined by measuring the distance between the two distal edges (66) of the back waist region, between the clamps. Five specimens of each code are analyzed, and the results for each code are averaged.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A folded, open, absorbent garment, comprising:
an absorbent chassis including an absorbent core positioned between an outer cover and a body side liner, the absorbent chassis defining a waist opening and first and second leg openings when in a fastened position;
the absorbent chassis having a longitudinal length extending from a front waist region to a back waist region, with each of two transversely opposed distal edges of the back waist region folded onto a surface of the absorbent chassis along respective longitudinal fold lines, and each of two transversely opposed distal edges of the front waist region folded onto a surface of the absorbent chassis along respective longitudinal fold lines, and the absorbent chassis folded along at least one transverse fold line;
wherein a width between the longitudinal fold lines in the back waist region is less than the combined widths between each of the transversely opposed distal edges of the back waist region and the respective longitudinal fold line; and
the width between the longitudinal fold lines in the back waist region is greater than a width between transversely opposed leg elastics in a crotch region of the absorbent chassis, such that the transversely opposed leg elastics are positioned between the longitudinal fold lines in at least a portion of the garment.

2. The folded absorbent garment of claim 1, wherein the longitudinal fold lines in the back waist region are discontinuous with the longitudinal fold lines in the front waist region.

3. The folded absorbent garment of Claim 1, wherein portions of transversely opposed distal edges of the crotch region are not folded onto a surface of the absorbent chassis.

4. The folded absorbent garment of claim 1, wherein a distance between the longitudinal fold lines in the back waist region is greater than a distance between transversely opposed distal edges in a crotch region of the absorbent chassis.

5. The folded absorbent garment of claim 1, wherein there are no longitudinal fold lines in the absorbent chassis between transversely opposed leg elastics in a narrowest width of a crotch region of the absorbent chassis.

6. The folded absorbent garment of claim 1, wherein the transversely opposed distal edges of the back waist region overlap one another on the surface of the absorbent chassis.

7. The folded absorbent garment of claim 1, wherein the absorbent chassis is folded along the at least one transverse fold line and thereby aligns the front waist region with the back waist region.

8. The folded absorbent garment of claim 1, wherein the absorbent chassis has an elasticized-crotch-to-waist ratio of about 0.35 or less with the elasticized-crotch-to-waist ratio being a narrowest distance between two transversely opposed leg elastics in a crotch region of the absorbent chassis divided by an expanded width of the absorbent chassis between the transversely opposed distal edges of the back waist region.

9. The folded absorbent garment of claim 1, wherein the absorbent chassis has a crotch-to-waist ratio of about 0.55 or less with the crotch-to-waist ratio being a narrowest distance between transversely opposed distal edges in a crotch region of the absorbent chassis divided by an expanded width of the absorbent chassis between the transversely opposed distal edges of the back waist region.

10. The folded absorbent garment of claim 1, wherein the absorbent chassis comprises an absorbent core positioned between an outer cover and a body side liner, and the absorbent chassis has an absorbent-to-waist ratio of about 0.47 or less with the absorbent-to-waist ratio being a widest width of the absorbent core divided by an expanded width of the absorbent chassis between the transversely opposed distal edges of the back waist region.

11. The folded absorbent garment of claim 1, wherein the garment is packaged in the folded position.

12. A folded, open, absorbent garment, comprising:
an absorbent chassis including an absorbent core positioned between an outer cover and a body side liner, the absorbent chassis defining a waist opening and first and second leg openings when in a fastened position;

the absorbent chassis having a longitudinal length extending from a front waist region to a back waist region, with each of two transversely opposed distal edges of the back waist region folded onto a surface of the absorbent chassis along respective longitudinal fold lines, and each of two transversely opposed distal edges of the front waist region folded onto a surface of the absorbent chassis along respective longitudinal fold lines, and the absorbent chassis folded along at least one transverse fold line;

wherein the absorbent chassis has an elasticized-crotch-to-waist ratio of about 0.35 or less with the elasticized-crotch-to-waist ratio being a narrowest distance between two transversely opposed leg elastics in a crotch region of the absorbent chassis divided by the sum of an expanded width of the absorbent chassis between the transversely opposed distal edges of the back waist region.

13. The folded absorbent garment of claim 12, wherein a distance between the longitudinal fold lines in the back waist region is greater than the narrowest distance between the two transversely opposed leg elastics in the crotch region of the absorbent chassis.

14. The folded absorbent garment of claim 12, wherein the longitudinal fold lines in the back waist region are discontinuous with the longitudinal fold lines in the front waist region.

15. The folded absorbent garment of claim 12, wherein portions of transversely opposed distal edges of the crotch region are not folded onto a surface of the absorbent chassis.

16. The folded absorbent garment of claim 12, wherein the transversely opposed distal edges of the back waist region overlap one another on the surface of the absorbent chassis.

17. The folded absorbent garment of claim 12, wherein the garment is packaged in the folded position.

18. The folded absorbent garment of claim 12, wherein the absorbent chassis has an elasticized-crotch-to-waist ratio of about 0.3 or less.

19. The folded absorbent garment of claim 12, wherein the absorbent chassis has an elasticized-crotch-to-waist ratio of about 0.25 or less.

20. The folded absorbent garment of claim 12, wherein the absorbent chassis has an elasticized-crotch-to-waist ratio of about 0.15 or less.

21. A folded, open, absorbent garment, comprising:
an absorbent chassis including an absorbent core positioned between an outer cover and a body side liner, the absorbent chassis defining a waist opening and first and second leg openings when in a fastened position;
the absorbent chassis having a longitudinal length extending from a front waist region to a back waist region, with each of two transversely opposed distal edges of the back waist region folded onto a surface of the absorbent chassis along respective longitudinal fold lines, and each of two transversely opposed distal edges of the front waist region folded onto a surface of the absorbent chassis along respective longitudinal fold lines, and the absorbent chassis folded along at least one transverse fold line;
wherein the absorbent chassis has a crotch-to-waist ratio of about 0.55 or less with the crotch-to-waist ratio being a narrowest distance between transversely opposed distal edges in a crotch region of the absorbent chassis divided by an expanded width of the absorbent chassis between the transversely opposed distal edges of the back waist region.

22. The folded absorbent garment of claim 21, wherein a distance between the longitudinal fold lines in the back waist region is greater than the narrowest distance between the two transversely opposed leg elastics in the crotch region of the absorbent chassis.

23. The folded absorbent garment of claim 21, wherein the longitudinal fold lines in the back waist region are discontinuous with the longitudinal fold lines in the front waist region.

24. The folded absorbent garment of claim 21, wherein portions of transversely opposed distal edges of the crotch region are not folded onto a surface of the absorbent chassis.

25. The folded absorbent garment of claim 21, wherein the transversely opposed distal edges of the back waist region overlap one another on the surface of the absorbent chassis.

26. The folded absorbent garment of claim 21, wherein the garment is packaged in the folded position.

27. The folded absorbent garment of claim 21, wherein the absorbent chassis has a crotch-to-waist ratio of about 0.45 or less.

28. The folded absorbent garment of claim 21, wherein the absorbent chassis has a crotch-to-waist ratio of about 0.35 or less.

29. The folded absorbent garment of claim 21, wherein the absorbent chassis has a crotch-to-waist ratio of about 0.25 or less.

30. A folded, open, absorbent garment, comprising:
an absorbent chassis including an absorbent core positioned between an outer cover and a body side liner, the absorbent chassis defining a waist opening and first and second leg openings when in a fastened position;
the absorbent chassis comprising an absorbent core positioned between an outer cover and a body side liner, and having a longitudinal length extending from a front waist region to a back waist region, with each of two transversely opposed distal edges of the back waist region folded onto a surface of the absorbent chassis along respective longitudinal fold lines, and each of two transversely opposed distal edges of the front waist region folded onto a surface of the absorbent chassis along respective longitudinal fold lines, and the absorbent chassis folded along at least one transverse fold line;
wherein the absorbent chassis has an absorbent-to-waist ratio of about 0.47 or less with the absorbent-to-waist ratio being a widest width of the absorbent core divided by an expanded width of the absorbent chassis between the transversely opposed distal edges of the back waist region.

31. The folded absorbent garment of claim 30, wherein a distance between the longitudinal fold lines in the back waist region is greater than the narrowest distance between the two transversely opposed leg elastics in the crotch region of the absorbent chassis.

32. The folded absorbent garment of claim 30, wherein the longitudinal fold lines in the back waist region are discontinuous with the longitudinal fold lines in the front waist region.

33. The folded absorbent garment of claim 30, wherein portions of transversely opposed distal edges of the crotch region are not folded onto a surface of the absorbent chassis.

34. The folded absorbent garment of claim 30, wherein the transversely opposed distal edges of the back waist region overlap one another on the surface of the absorbent chassis.

35. The folded absorbent garment of claim 30, wherein the garment is packaged in the folded position.

36. The folded absorbent garment of claim 30, wherein the absorbent chassis has an absorbent-to-waist ratio of about 0.42 or less.

37. The folded absorbent garment of claim 30, wherein the absorbent chassis has an absorbent-to-waist ratio of about 0.37 or less.

38. The folded absorbent garment of claim 30, wherein the absorbent chassis has an absorbent-to-waist ratio of about 0.27 or less.

39. A method of folding an open absorbent garment, comprising:

providing an absorbent chassis including an absorbent core positioned between an outer cover and a body side liner, the absorbent chassis having a longitudinal length extending from a front waist region to a back waist region;

folding each of two transversely opposed distal edges of the back waist region onto a surface of the absorbent chassis along respective longitudinal fold lines;

folding each of two transversely opposed distal edges of the front waist region onto a surface of the absorbent chassis along respective longitudinal fold lines, wherein a distance between the longitudinal fold lines in the back waist region is greater than a distance between transversely opposed leg elastics in a crotch region of the absorbent chassis; and     folding the absorbent chassis along at least one transverse fold line.

\* \* \* \* \*